United States Patent [19]

Kern et al.

[11] 4,233,236

[45] Nov. 11, 1980

[54] SEPARATION OF SULPHONIC ACIDS FROM THE MEDIUM IN WHICH THEY ARE PREPARED

[75] Inventors: René Kern, Savigny-sur-Orge; Daniel Augustin, Massy, both of France

[73] Assignee: ATO Chimie, Paris, France

[21] Appl. No.: 972,726

[22] Filed: Dec. 26, 1978

[30] Foreign Application Priority Data

Dec. 28, 1977 [FR] France .................... 77 39485

[51] Int. Cl.$^3$ ................. C07C 139/00; C07C 143/24
[52] U.S. Cl. ............................ 260/504 S; 260/513 R
[58] Field of Search ..................... 260/513 R, 504 S

[56] References Cited

U.S. PATENT DOCUMENTS 3,454,479  7/1969  Hopkins et al. ................ 260/513 R

*Primary Examiner*—Alan Siegel
*Attorney, Agent, or Firm*—Ostrolenk, Faber, Gerb & Soffen

[57] ABSTRACT

A process for the separation of sulphonated paraffins from their sulphonation medium, which comprises neutralization of the sulphuric acid present and separation into two phases, the lower phase containing the sulphate. The neutralization is carried out in such a way that only a part of the sulphuric acid is neutralized. A hydrocarbon is added, which dissolves the sulphonated and non-sulphonated paraffins and forms with water, an azeotropic mixture which is distilled in order to remove all or a part of the water present. The process allows the separation of sulphonates which are purer than in the past and which are poor in sulphates, while the sulphate layer contains only very little sulphonic acid.

12 Claims, No Drawings

SEPARATION OF SULPHONIC ACIDS FROM THE MEDIUM IN WHICH THEY ARE PREPARED

The present invention relates to a process for the separation of sulphonic acids from the aqueous reaction medium in which they are produced by the sulphonation of paraffins. The aim of the invention is, in particular, the removal of sulphuric acid from this medium. The invention is applicable in a general manner to mixtures obtained in the sulphonation of paraffins and, in particular, to those resulting from the simultaneous action of sulphurous anhydride and oxygen on paraffin hydrocarbons in the presence of catalysts or of photochemical radiation.

In view of the industrial importance of surface active agents based on sulphonated paraffins, sulphonation and subsequent separation of the sulphonated derivatives formed has been the subject of a great deal of work. However, the separation of the useful products has not been entirely satisfactory up to the present: the different processes proposed always lead to sulphonates which are still too impure, having too high a content of sulphate, while the by-products separated, principally sulphates of alkali metals, still contain substantial amounts of sulphonates, thus reducing the yield of the process. This is the case with processes in which the neutralization of sulphuric acid is effected by means of an alkaline hydroxide, with preliminary separation of the aqueous and organic phases by the addition of alcohols or organic extraction solvents. Other processes in which separation is effected by means of polar solvents lead to products which are no purer. The known process which comprises heating the crude reaction mixture to 180° C. in order to cause separation into two layers has the disadvantage of leading to degradation of the sulphonic acids and colouration thereof; a subsequent decolourizing operation is therefore required.

The object of the present invention is to provide an improved process which will allow enhanced separation of the products of sulphonation to be obtained in a relatively simple manner, while leaving in the sulphonates, a lesser amount of sulphate than was allowed by the prior art; this process has the further advantage that very little sulphonic acid is lost in the form of sulphonates retained in the by-product which is separated. The latter is generally in the form of an aqueous solution, which simplifies separation thereof since filtration is unnecessary. The sulphonates thus produced are colourless and substantially free of organic impurities.

Unlike most of the known processes in which, after separation of the greater part of the paraffins which have not reacted, complete neutralization of the sulphuric acid present in the reaction medium takes place before separation of the by-product, the new process according to this invention comprises partial neutralization: thus the sulphuric acid present is converted into the acid sulphate of an alkali metal or of ammonium, or into a mixture of acid sulphate and neutral sulphate and/or sulphuric acid, the mixture being definitely acid. This step, which leads to good separation of the organic phase containing the sulphonic acids and the aqueous phase containing the partially neutralized sulphuric acid, results in much improved separation of the sulphuric acid and the sulphonic acids produced; the sulphonates obtained contain less than 3% of sulphates.

Moreover, this improved separation is accompanied by some economy of the base used for neutralizing the sulphuric acid, while in the prior art, one equivalent of the base is generally used for one equivalent of sulphuric acid, in the process of the invention usually not more than 0.2 to 0.8 equivalents of base is used for one equivalent of acid. Sodium hydroxide is the alkali metal base most usually employed, because it is the most economic, but nevertheless the cost thereof is not negligible; when operating in accordance with the invention, about a half quantity will suffice, that is to say 0.5 equivalents or even less, for 1 equivalent of $H_2SO_4$; in this way the acid is converted into bisulphate or into a mixture of acid and bisulphate, which is easier to separate than neutral sulphate. Although sodium hydroxide is the neutralizing agent most commonly employed, it is possible to use other hydroxides such as those of potassium, ammonium or lithium; the use of any of these hydroxides is possible within the scope of the invention, in accordance with different modifications thereof; the oxides and carbonates of alkali metals can also be used as neutralizing agents.

According to the invention, the reaction medium has added thereto a hydrocarbon chosen from those which dissolve both sulphonated and non-sulphonated paraffins and which are capable of forming an azeotropic mixture with water. This addition is followed by distillation to remove all or part of the water present in the reaction medium; this operation leads to the formation of two phases, one of which is an organic phase containing the sulphonic acids and non-sulphonated paraffins while the other contains the acid sulphate resulting from the partial neutralization. The physical separation of these two phases leads to better results than the similar separation which takes place in the prior art.

Particularly suitable as the hydrocarbons to be added, as referred to above, are aliphatic, cycloaliphatic and aromatic hydrocarbons, preferably those whose boiling points are between 35° and 140° C., and most preferably between 60° and 100° C. These include, by way of non-limitative example, pentanes, octanes, cyclohexane, methyl-cyclohexane, benzene, toluene, xylenes etc.

The removal of water by azeotropic distillation, in accordance with the invention, may be effected according to two different modes of operation. In the first, the hydrocarbon is added at the beginning, before or during the partial neutralization which moreover, is facilitated by this dilution, since the hydrocarbon increases the insolubility of the salt; the distillation of the azeotropic mixture formed by this hydrocarbon and the water of the reaction mixture is then effected immediately after neutralization. The other mode of operation consists in removing a substantial part of the water by distillation, preferably under vacuum, using the reaction medium after neutralization; the hydrocarbon is added only after this first operation and addition thereof is followed by azeotropic distillation which removes the remainder of the water; this enables the quantity of azeotropic mixture which has to be distilled to be reduced since less water remains to be removed. The proportion of hydrocarbon to be added to the reaction solution containing the sulphonic acids is in general from 1 to 6 parts and preferably from 2 to 3 parts by weight, for one part of reaction solution. It is important to remove the maximum amount of water so that the sulphonic phase itself will retain the least possible amount so that its content of sulphates will be small.

The azeotropic distillation of the water-solvent mixture may be effected at atmospheric pressure; it can also be effected under reduced pressure, which lowers the boiling point of the azeotropic mixture and thus lowers the temperature at which the reaction mass is treated, thereby avoiding the risk of colouration of the sulphonic acids; distillation can also be carried out under slight pressure in order to increase the water-content of the azeotropic mixture and to reduce the duration of the operation.

Given that the distillation temperture of the azeotropic mixture increases, as the amount of water removed increases, one practical way of determining the stage which this distillation has reached is by monitoring the temperature.

As soon as the separation into two phases has been carried out after the azeotropic distillation, the lower layer containing the acid sulphate is separated; the upper organic layer is neutralized, generally by means of sodium hydroxide, so as to convert the sulphonic acids into sulphonates; this is then subjected to distillation under reduced pressure in order to evaporate the remainder of the hydrocarbons and the non-sulphonated paraffins, which leaves as a residue, the sulphonated paraffins which have been formed.

The process according to the invention, which consists, after the separation of the greater part of the paraffins which have not reacted, in the partial neutralization of the sulphuric acid with the possible addition of a solvent, the removal of the water by azeotropic distillation from the water-solvent mixture and the separation into two phases, namely an organic phase containing the sulphonic acids and another phase containing the partially neutralized sulphuric acid, can be carried out according to different modes of operation, depending on the alkaline hydroxide which is used.

When sodium hydroxide is used as the neutralizing agent, it is preferable to add the quantity of sodium hydroxide appropriate to the formation of sodium acid sulphate, that is to say 0.5 equivalent of sodium hydroxide for 1 equivalent of sulphuric acid and to distil only a part of the water, leaving in the medium 1 mole of water for 1 mole of sulphuric acid, that is to say the quantity of water necessary for the formation of the monohydrate of sodium acid sulphate. In fact, since the melting point of the salt is 58° C., it is in the molten state at the operating temperature and there is excellent separation into two layers: an organic layer containing the sulphonic acids and less than 3% of sulphate and a liquid layer containing the monohydrate of sodium acid sulphate substantially free of sulphonic acids. Moreover, the quantity of sodium hydroxide which has to be added can be less than 0.5 equivalents per equivalent of sulphuric acid.

When potassium hydroxide is used as the neutralizing agent, the sulphuric acid can be partially neutralized in the form of potassium acid sulphate, or better in the form of a mixture of potassium acid sulphate and sulphuric acid, by the addition of 0.5 equivalent or less of potassium hydroxide per equivalent of sulphuric acid.

Although the potassium acid sulphate or the mixture thereof with sulphuric acid does not have, as in the case of sodium sulphate monohydrate, a melting point lower than the distillation temperature of the water-solvent azeotrope, and although its solubility in water is poor, it is found that the separation of the organic phase containing the sulphonic acids and the heterogeneous phase containing the crystallized potassium acid sulphate is good; moreover, the potassium acid sulphate is readily filtrable. In this case, one can either leave a certain amount of water in the medium or it can be eliminated entirely.

In the case where ammonium hydroxide is used, since the acid salt of ammonium is highly soluble in water and particularly in warm water, it is possible to distil the major part of the water and to obtain two liquid phases which separate readily: an organic phase containing the sulphonic acids and an aqueous phase containing the ammonium acid sulphate in solution.

The invention is illustrated by the following non-limitative examples.

Examples 1 to 5 concern the separation of the product obtained in a photochemical reactor supplied with a mixture of linear $C_{14}$ and $C_{15}$ paraffins, with water, with sulphurous anhydride and with oxygen, after degasing and separation by decantation of a part of the excess paraffins; the reaction mixture treated had the following percentage composition by weight:
sulphonic acids:24
sulphuric acid:9.8
non-sulphonated paraffins:24.5
water:41.7

EXAMPLE 1

To 100 g of the above-mentioned mixture, there is added 300 g of cyclohexane and 20 g of an aqueous 20% solution of sodium hydroxide; in other words, 4 g of NaOH, that is to say 0.1 equivalent, is used to neutralize 9.8 g $H_2SO_4$ (0.2 equivalent) which means that the sulphuric acid is neutralized to the sodium bisulphate stage. The mixture obtained is heated in a one liter flask fitted with a Dean Stark apparatus with an ascending cooler above it.

The mixture which commences to distil at 69.8° C. is constituted by an azeotropic mixture of 91.5% cyclohexane with 8.5% water. After condensation in the cooler, the water is collected in the Dean Stark apparatus, while the cyclohexane which is separated returns to the flask containing the reaction mixture.

The azeotropic distillation is continued until 57.7 g of water is collected. The reaction mixture separates into two liquid layers: a light cyclohexane phase which contains the sulphonic acids and the non-sulphonated paraffins and a heavy aqueous phase containing the sodium bisulphate.

The heavy aqueous bisulphate phase solidifies on cooling. It is washed with 50 ml of cyclohexane; the washing liquid is added to the light phase in order to recover the organic products which it contains, namely about 0.5% of sulphonic acids. There is collected finally 13.5 g of a solid whose composition corresponds to the overall formula: $NaHSO_4.1H_2O$ with a melting point of about 56° C. This acid sulphate does not contain any organic matter; there is therefore no loss of sulphonates into the heavy phase.

The light organic phase is neutralized with 20% aqueous sodium hydroxide, after which it is subjected to distillation; the non-sulphonated paraffins, the cyclohexane and the water distil and there remains 26 g of a pasty residue constituted by sodium sulphonates containing only 1% of $Na_2SO_4$.

EXAMPLE 2

One proceeds exactly as in Example 1, except that the azeotropic distillation is terminated when 47 g of water has been removed as against 57.7 g in Example 1. In these conditions, there is 23.5 g of heavy phase constituted by an aqueous solution of sodium bisulphate.

From the light phase, there is obtained 25.7 g of sulphonates containing 2% of $Na_2SO_4$.

EXAMPLE 3

The procedure of Example 1 is repeated with 300 g of xylene in place of the cyclohexane, and the azeotropic distillation takes place at 65° C. under reduced pressure. The quantity of water removed by this distillation is 57.5 g and the separation into two layers takes place exactly as in Example 1. This operation enables 25.8 g of sodium sulphonates to be recovered, containing 1.3% of $Na_2SO_4$. The heavy phase, after washing with 50 ml of cyclohexane, leaves a precipitate of 13.4 g of $NaHSO_4.1H_2O$ containing 0.3% of sulphonic acids.

EXAMPLE 4

Treatment is effected according to the second mode of operation, which comprises a preliminary distillation before the addition of hydrocarbon. The operation takes place in a conventional distillation apparatus comprising a 500 ml flask fitted with a stirrer, a thermometer, a Vigreux column, a cooler and a receiving flask. 100 g of the same reaction mixture as in Examples 1 and 2 is subjected to distillation in this apparatus, after having undergone partial neutralization with 20 g of an aqueous 20% solution of sodium hydroxide (that is to say 0.1 equivalent NaOH for 0.2 equivalent $H_2SO_4$ present in the mixture). Distillation with stirring and under a reduced pressure of 20 mm Hg enabled 45 g of water to be collected in the receiving flask. The remaining reaction mixture was then placed in the same apparatus as was used in Example 1; after adding 300 g of cyclohexane, azeotropic distillation was effected as in Example 1. 12.5 g of water was thus recovered and the contents of the flask separated into two liquid phases. The upper organic phase yielded, when neutralized with aqueous sodium hydroxide and after removal of the volatile matter by distillation, 25.8 g of sodium sulphonates containing 0.9% of $Na_2SO_4$, that is to say less than in the preceding examples. The heavy phase is washed with 50 ml of cyclohexane and solidifies at ambient temperature, to form 13.4 g of a product whose composition corresponds to sodium acid sulphate monohydrate.

EXAMPLE 5

The mode of operation is the same as in Example 1, except that neutralization is effected with only 10 g of 20% sodium hydroxide, that is to say 0.05 equivalent for 0.2 equivalent of $H_2SO_4$ present in the mixture treated. After distillation of the azeotropic mixture of cyclohexane-water, 47.7 g of water is recovered, which leads to separation of the two liquid phases. The light phase when treated as in the preceding examples yields 25.7 g of sodium sulphonates containing 1.2% of $Na_2SO_4$. The heavy phase when washed with 50 ml of cyclohexane with heating yields, after removal of the cyclohexane, 13.2 g of a solid mixture corresponding to the composition:

$NaHSO_4.H_2SO_4$ and 3 moles of water

EXAMPLE 6

In the same apparatus as in Example 1, there is treated 100 g of a crude mixture of sulphonic acids having the following percentage composition by weight:
sulphonic acids:30
sulphuric acid:6.8
non-sulphonated paraffins:35
water:28.2

300 g of cyclohexane is added and partial neutralization is effected with 19.4 g of a 20% aqueous solution of potassium hydroxide; in other words 3.88 g KOH, that is to say 0.0694 equivalent, is employed to neutralize the 6.8 g=0.1388 equivalent of sulphuric acid present; thus neutralization is carried out with 0.5 equivalent KOH for 1 equivalent $H_2SO_4$. The azeotropic distillation of the cyclohexane-water mixture removes 37.2 g of water and this immediately causes separation into two phases. The light phase is neutralized with 20% aqueous potassium hydroxide and is then subjected to distillation under reduced pressure in order to evaporate the non-sulphonated paraffins, the water and the cyclohexane; this yields a residue of 34.5 g of potassium sulphonates (theoretical amount 34.8 g) containing 5.2% of $K_2SO_4$. The heavy phase when washed with 50 ml cyclohexane yields 15.6 g of a solution containing for the most part, potassium bisulphate and including 0.4% of sulphonic acid.

EXAMPLE 7

The mode of operation described in Example 1 is used; partial neutralization is effected with only 9.7 g of 20% potassium hydroxide, that is to say 0.0347 equivalent KOH for 0.1388 equivalent of sulphuric acid present, that is to say 0.25 equivalent KOH for 1 equivalent $H_2SO_4$. After distillation of the cyclohexane-water azeotropic mixture, 30 ml of water is recovered which causes separation of two liquid phases. The light phase is treated as in the preceding examples; this yields 34.6 g of potassium sulphonates containing 3% of potassium sulphate. The heavy phase is washed with 50 ml of cyclohexane with heating and, after removal of the solvent, this yields 13.8 g of a crystallized mixture constituted by $H_2SO_4$, $KHSO_4$ and water.

EXAMPLE 8

The mode of operation used is that described in Example 1; partial neutralization is effected with ammonium hydroxide. 24.3 g or 10% ammonium hydroxide, that is to say 0.0694 equivalent, is used to neutralize 6.8 g=0.1388 equivalent of sulphuric acid present, that is to say 0.5 equivalent $NH_4OH$ for 1 equivalent $H_2SO_4$. The azeotropic distillation removes 49.0 g of water, which causes separation into two liquid phases. The light phase is neutralized with aqueous sodium hydroxide and treated as in the preceding examples. 34.6 g of sodium sulphonates is recovered containing 2% of sodium sulphate. The heavy aqueous phase weighs 8.8 g; it is a solution in water of $NH_4HSO_4$ containing less than 0.8% of sulphonic acids.

EXAMPLE 9

In the same apparatus as in Example 1, there is treated 100 g of a crude mixture of sulphonic acids of the same composition as that referred to in Example 6. 300 g of cyclohexane is added and neutralization is effected with 19.4 g of a 20% aqueous solution of potassium hydroxide, that is to say 0.069 equivalent to neutralize 6.8 g of sulphuric acid, namely 0.138 equivalent, that is to say 0.5 equivalent KOH for 1 equivalent $H_2SO_4$. All of the water is removed by taking it up azeotropically; the mixture then comprises a liquid phase containing in suspension a precipitate of 9.1 g of potassium acid sulphate which is separated by filtration. The cyclohexane phase is neutralized with an aqueous solution of sodium hydroxide and the sodium sulphonates are separated in accordance with the method previously described; 32 g of sulphonates is separated, containing 0.44% of potassium sulphate.

Similar results are obtained with initial mixtures containing 20 to 40% of sulphonic acids, 5 to 15% of sulphuric acid, 20 to 40% of non-sulphonated paraffins and 20 to 50% of water.

EXAMPLE 10

The operations of example 1 are repeated the starting mixture comprising n-dodecane sulfonic acid instead of the $C_4$–$C_{15}$ sulfonic acids. The same results are obtained.

EXAMPLE 11

In example 4, the starting sulfonic acids are replaced by n-octadecane sulfonic acid; the results are the same as in example 4.

We claim:

1. Process for the separation of sulfonated paraffins from the aqueous reaction mixture in which they are produced by sulfonation of paraffins, said reaction mixture containing sulfuric acid, unsulfonated paraffins and a hydrocarbon solvent for said sulfonated and unsulfonated paraffins which is capable of forming azeotropic mixture with water which comprises: partially neutralizing the sulfuric acid present in the reaction mixture to form bisulfate; subjecting the reacting mixture to a distillation to remove at least a substantial part of the water in the form of azeotropic mixture with the hydrocarbon; allowing the remaining material to separate into two layers, and separating the bottom layer, which contains bisulfate, from the upper sulfonic acid containing layer.

2. Process according to claim 1, in which the amount of solvent which is added to the sulphonated paraffins is controlled in such a way that the azeotropic distillation removes the major part of the water present.

3. Process according to claim 1, in which the amount of solvent which is added to the sulphonated paraffins is controlled in such a way that the azeotropic distillation removes substantially completely the water present.

4. Process according to claim 2, wherein the hydrocarbon is added and the azeotropic distillation is effected after the removal of a substantial part of the water by distillation carried out on the partially neutralized reaction mixture.

5. Process according to claims 2, wherein the physical separation of the two layers takes place after the removal of the major part of the water by azeotropic distillation.

6. Process according to claim 1, in which the neutralizing agent used is sodium hydroxide, and after partial neutralization to form bisulphate and after azeotropic distillation, there remains in the reaction mixture the amount of water necessary for the formation of the monohydrate of the bisulphate.

7. Process according to claim 1, in which the neutralizing agent used is potassium hydroxide, and after partial neutralization to form a mixture of the bisulphate and sulphuric acid, and after the azeotropic distillation, there is left in the reaction mixture a quantity of water less than that required to dissolve the acid salt.

8. Process according to claim 3, in which the neutralizing agent used is potassium hydroxide, and after partial neutralization to form a mixture of bisulphate and sulphuric acid, the azeotropic distillation is effected to remove all of the water.

9. Process according to claim 2, in which the neutralizing agent used is ammonium hydroxide, and after partial neutralization to form ammonium bisulphate, the azeotropic distillation is so carried out that there remains in the medium the precise amount of water necessary to dissolve the bisulphate.

10. Process according to claim 1, wherein the organic layer, containing the sulphonic acids, is neutralized with a base, after which it is subjected to distillation under reduced pressure, which leaves as a residue, the sulphonates produced.

11. Process according to claim 1, wherein the lower layer containing the bisulphate is washed with hydrocarbon in order to recover the sulphonic acids which it may contain, and the washing liquid is added to the organic layer.

12. Process for the separation of sulphonated paraffins according to claim 1, wherein the partial neutralization of the reaction mixture is made with 0.2 to 0.8 equivalents of a base for each 1 equivalent of $H_2SO_4$ present.

* * * * *